United States Patent [19]

Diana et al.

[11] 4,140,860
[45] Feb. 20, 1979

[54] BRIDGED-BIS-HYDROXYAMIDE DICARBANILATES

[75] Inventors: Guy D. Diana, Stephentown; Royal A. Cutler, Sand Lake, both of N.Y.

[73] Assignee: Sterling Drug Inc., New York, N.Y.

[21] Appl. No.: 916,345

[22] Filed: Jun. 16, 1978

Related U.S. Application Data

[60] Division of Ser. No. 833,485, Jul. 15, 1977, Pat. No. 4,119,668, which is a division of Ser. No. 739,447, Nov. 8, 1976, Pat. No. 4,085,114, which is a division of Ser. No. 582,646, Jun. 2, 1975, Pat. No. 4,022,833, which is a division of Ser. No. 332,267, Feb. 14, 1973, Pat. No. 3,928,427, which is a continuation-in-part of Ser. No. 123,097, Mar. 10, 1971, abandoned.

[51] Int. Cl.² .................... C07C 125/06; A61K 31/27
[52] U.S. Cl. ................................................. 560/29
[58] Field of Search ........................... 560/12, 22, 29

[56] References Cited

U.S. PATENT DOCUMENTS 3,524,883  8/1970  Kersnar et al. ...................... 260/584

OTHER PUBLICATIONS

Sterling, Chem. Absts., 84, 164137(k), 1976.

Primary Examiner—James O. Thomas, Jr.
Assistant Examiner—G. T. Breitenstein
Attorney, Agent, or Firm—Theodore C. Miller; B. Woodrow Wyatt

[57] ABSTRACT

N,N'-Bridged-bis[(O and/or N-substituted)-2-alkyl-2-hydroxyethylamines] of the formula

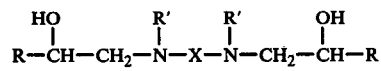

are prepared by condensing an epoxide of the formula

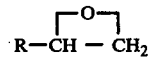

and a diamine of the formula R'NH—X—NHR'. The products and dicarbanilates, acid-addition salts, N,N'-dioxides and N,N'diammonium quaternary salts derived therefrom have antibacterial activity in vitro and are useful as antibacterial agents.

3 Claims, No Drawings

BRIDGED-BIS-HYDROXYAMIDE DICARBANILATES

CROSS-REFERENCE TO RELATED APPLICATIONS

This application is a division of our copending application Ser. No. 833,485, filed Sept. 15, 1977, now U.S. Pat. No. 4,119,668, which is a division of our copending application Ser. No. 739,447, filed Nov. 8, 1976, now U.S. Pat. No. 4,085,114, which is a division of our copending application Ser. No. 582,646, filed June 2, 1975, now U.S. Pat. No. 4,022,833, which is a division of our copending application Ser. No. 332,267, filed Feb. 14, 1973, now U.S. Pat. No. 3,928,427, which is a continuation-in-part of our copending application Ser. No. 123,097, filed Mar. 10, 1971 and now abandoned.

FIELD OF THE INVENTION

This invention relates to compositions of matter classified in the art of organic chemistry as N,N'-bridged-bis[(O and/or N-substituted)-2-alkyl-2-hydroxyethylamines] and to a process for preparing them.

SUMMARY OF THE INVENTION

In its composition of matter aspect our invention provides N,N'-(X)-bis[N-(R')-2-(R)-2-(ZO)-ethylamine] of the formula

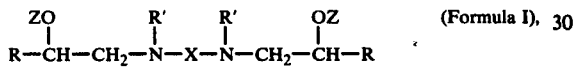 (Formula I), wherein:
R is alkyl of three to fifteen carbon atoms or cycloalkyl of four to seven ring carbon atoms;
R' is hydrogen or a tertiary alkyl of one to four carbon atoms;
X is alkylene of two to twelve carbon atoms with bonds to the nitrogen atoms at different carbon atoms or X'-Y-X", wherein X' and X" are alkylene of one to four carbon atoms with bonds to Y and to the nitrogen atoms at the same or different carbon atoms and Y is cycloalkylene of four to seven ring carbon atoms with bonds to X' and X" at the same or different carbon atoms, phenylene, vinylene or ethynylene;
the sum of the number of carbon atoms of R and X is at least nine;
Z is hydrogen or, when R' is a tertiary alkyl of one to four carbon atoms, N-phenylcarbamoyl or N-phenylcarbamoyl substituted in the benzene ring by one to three members selected from the group consisting of a tertiary alkyl of one to four carbon atoms, halo and a tertiary alkoxy of one to four carbon atoms or by a member selected from the group consisting of trifluoromethyl, acetamido, nitro, and methylsulphonyl;
acid-addition salts thereof; and,
when R' is a tertiary alkyl of one to four carbon atoms and Z is hydrogen, N,N'-dioxides, N,N'-di(a tertiary alkyl of one to four carbon atoms)diammonium quaternary salts and N,N'-dibenzyldiammonium quaternary salts thereof.

The compounds of Formula I and acid-addition salts, N,N'-dioxides and N,N'-diammonium quaternary salts thereof have antibacterial activity in vitro and are useful as antibacterial agents.

In its process aspect our invention provides the process for preparing N,N'-(X)-bis[N-(R')-2-(R)-2-(ZO)-ethylamine] of Formula I, wherein Z is hydrogen, which comprises condensing an epoxide of the formula

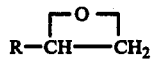 (Formula II)

with a diamine of the formula

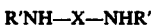 (Formula III), wherein R of Formula II and R' and X of Formula III have the same meanings ascribed thereto in Formula I.

DETAILED DESCRIPTION OF THE INVENTION

When R is alkyl of three to fifteen carbon atoms, it is normal alkyl or branched alkyl as illustrated by propyl, isopropyl, butyl, isobutyl, sec-butyl, tert-butyl, pentyl, hexyl, heptyl, octyl, nonyl, decyl, undecyl, dodecyl, tridecyl, tetradecyl and pentadecyl. Since R and ethyl are integral, they are named integrally when R is alkyl. Thus, the illustrated alkyls become respectively, pentyl, 3-methylbutyl, hexyl, 4-methylpentyl, 2-methylpentyl, 3,3-dimethylbutyl, heptyl, octyl, nonyl, decyl, undecyl, dodecyl, tridecyl, tetradecyl, pentadecyl, hexadecyl and heptadecyl.

When R is cycloalkyl of four to seven ring carbon atoms, it is cyclobutyl, cyclopentyl, cyclohexyl or cycloheptyl.

When R' is a tertiary alkyl of one to four carbon atoms, it is methyl, ethyl, propyl, isopropyl, butyl, isobutyl or sec-butyl.

When X is alkylene of two to twelve carbon atoms with bonds to the nitrogen atoms at different carbon atoms, it can be unbranched or branched. If unbranched, X is 1,2-ethylene, 1,3-propylene, 1,4-butylene, 1,5-pentylene, 1,6-hexylene, 1,7-heptylene, 1,8-octylene, 1,9-nonylene, 1,10-decylene, 1,11-undecylene or 1,12-dodecylene. If branched, X is, for example, 1,2-propylene, 2,4-butylene, 2,10-dodecylene, or 2-methyl-1,4-butylene.

When X is X'—Y—X", X' and X" can be the same or different and can be unbranched or branched alkylene of one to four carbon atoms with bonds to Y and to the nitrogen atoms at the same or different carbon atoms as illustrated by methylene, ethylene, ethylidene or 1,4-butylene. When Y is cycloalkylene of four to seven ring carbon atoms with bonds to X' and X" at the same or different carbon atoms, it is, for example, cyclobutylidene, 1,4-cyclohexylene or 1,2-cycloheptylene. When Y is cycloalkylene or vinylene, the bonds to X' and X" can be cis or trans. Thus, X'—Y—X" is, for example, 1,3-cyclobutylenebismethyl, 1,4-cyclohexylenebismethyl, cis-1,4-cyclohexylenebismethyl, trans-1,4-cyclohexylenebismethyl, 1,2-cycloheptylenebismethyl, cyclohexylene-1-methyl-4-(2-ethyl), cyclohexylene-1-methyl-4-(1-ethyl), cyclohexylene-1-methyl-4-(4-butyl), 1,4-phenylenebismethyl, trans-1,4-(2-butenylene) and 1,4-(2-butynylene).

When Z is N-phenylcarbamoyl substituted in the benzene ring, it is, for example, N-(o-tolyl)carbamoyl, N-(p-bromophenyl)carbamoyl, N-(m-methoxyphenyl)carbamoyl, N-(4-chloro-o-tolyl)carbamoyl, N-(5-chloro-2,4-dimethoxyphenyl)carbamoyl, N-[m-(trifluoromethyl)phenyl]carbamoyl, N-(p-acetamidophenyl)carbamoyl, N-(m-nitrophenyl)carbamoyl, or N-[p-(methylsulfonyl)phenyl]carbamoyl. Named as substituted carbanilates the illustrated substituted N-phenylcarbamoyls are, respectively, o-methylcarbanilate, p-bromocarbanilate, m-methoxycarbanilate, 2-methyl-4-chlorocarbanilate, 5-chloro-2,4-dimethoxycarbanilate, m-(trifluoromethyl)carbanilate, p-acetamidocarbanilate, m-nitrocarbanilate and p-(methylsulfonyl)carbanilate. When N-phenylcarbamoyl is substituted in the benzene ring by halo, halo is fluoro, chloro, bromo or iodo.

In N,N'-diammonium quaternary salts of the compounds of Formula I wherein R' is alkyl, atertiary alkyl of one to four carbon atoms can be methyl, ethyl, propyl, isopropyl, butyl, isobutyl or sec-butyl.

The manner and process of making and using the invention and the best mode of carrying it out will now be described so as to enable any person skilled in the art to which it pertains to make and use it.

The preferred method for carrying out the process of condensing an epoxide of Formula II with a diamine of Formula III is the use of a solvent inert under the reaction conditions, for example, acetonitrile, benzene, chloroform, N,N-dimethylformamide, ethanol, methanol or tetrahydrofuran at a temperature in the range of 0° to 100° C. Methanol is the preferred solvent and room temperature is the preferred temperature.

Compounds of Formula I in which R' is methyl are also prepared by methylating the corresponding compounds of Formula I in which R' is hydrogen with formaldehyde and formic acid.

Phenylcarbamoylation and phenylthiocarbamoylation of compounds of Formula I wherein R' is alkyl and Z is hydrogen, formation of acid-addition salts of the compounds of Formula I, and N,N'-dioxidation and N,N'-diquaternerization of the compounds of Formula I wherein R' is alkyl are all accomplished by standard methods.

The phenylisocyanates and phenylisothiocyanates required for phenylcarbamoylation and phenylthiocarbamoylation are known classes of compounds, some of which are commercially available. Those (substituted-phenyl)isocyanates which are not commercially available can be prepared, for example, by passing carbonyl chloride into hot solutions of the corresponding anilines in toluene, saturated with hydrogen chloride. Those (substituted-phenyl)isothiocyanates which are not commercially available can be prepared, for example, by treating the corresponding ammonium (substituted-phenyl) dithiocarbamates, prepared in turn from the corresponding substituted anilines, carbon disulfide and ammonia, with lead nitrate.

Acid-addition salts of the compounds of Formula I can be prepared with any pharmaceutically acceptable inorganic (mineral) or organic acid. If inorganic, the acid can be, for example, hydrochloric acid, hydrobromic acid, nitric acid, phosphoric acid or sulfamic acid. If organic, the acid can be, for example, acetic acid, glycolic acid, lactic acid, quinic acid, hydrocinnamic acid, succinic acid, tartaric acid, citric acid, methanesulfonic acid or benzenesulfonic acid.

N,N'-diammonium quaternary salts of compounds of Formula I wherein R' is alkyl can be prepared with any pharmaceutically acceptable atertiary one-to-four-carbon alkyl or benzyl ester of a strong inorganic or organic acid, for example, methyl chloride, methyl iodide, ethyl p-toluenesulfonate, propyl bromide, isobutyl iodide or benzyl bromide.

That the acid and the alkyl ester be pharmaceutically acceptable means that the beneficial properties inherent in the free base not be vitiated by side effects ascribable to the anions.

Although pharmaceutically acceptable salts are preferred, all salts are within the scope of the invention. A pharmaceutically unacceptable salt may be useful, for example, for purposes of identification or purification or in preparing a pharmaceutically acceptable salt by ion-exchange procedures.

The intermediate epoxides of Formula II are a known class of compounds. Their preparation is accomplished by epoxidation of the corresponding 1-alkenes and vinylcycloalkanes by any of several well-known methods, for example, by the use of peracetic acid buffered with sodium acetate. The 1-alkenes and vinylcycloalkanes are known compounds, some of which are commercially available.

The intermediate diamines of Formula III are also a known class of compounds, some of which are commercially available. Preparation of those which are not commercially available is accomplished by well-known methods, for example, by reductive amination of the corresponding diketone or dialdehyde, amination of the corresponding dihalide or dialcohol p-toluenesulfonate diester or reduction of the corresponding dinitrile, dioxime, diamide, diazide or other di-higher-oxidation-state nitrogen compound. Unsymmetrical diamines can be prepared from unsymmetrical starting materials.

The compounds of Formula I and acid-addition salts, N,N'-dioxides and N,N'-diammonium quaternary salts thereof are purified by distillation or by recrystallization. Their structures follow from their route of synthesis and are corroborated by infrared spectral analysis and by the correspondence of calculated and found values of elemental analysis of representative samples.

As stated above the compounds of Formula I and acid-addition salts, N,N'-dioxides and N,N'-diammonium quaternary salts thereof have antibacterial activity in vitro, which was determined by a standard serial dilution test. In this test the concentration of compound arresting the growth of the microorganism is the bacteriostatic concentration and is expressed in parts per million (p.p.m.). The concentration of compound preventing growth of the microorganism after further incubation is the bactericidal concentration and is also expressed in parts per million.

The compounds of Formula I and acid-addition salts, N,N'-dioxides and N,N'-diammonium quaternary salts thereof are useful as antibacterial agents and are especially useful for disinfecting and sanitizing living and non-living surfaces by conventional swabbing, padding, spraying, immersing, rinsing and the like techniques. Depending on the particular purpose involved, the compounds are used in aqueous solution, in aqueous detergent solutions or in solutions in organic solvents.

The following examples illustrate specific embodiments of our invention without limiting the latter thereto.

EXAMPLE 1

A solution of 1-undecene oxide (88.8 g.), hexamethylenediamine (1,6-hexanediamine, 30.3 g.) and methanol (400 ml.) was allowed to stand at 0° C. overnight, then at room temperature over the weekend. The solid was collected and recrystallized from ethanol, affording N,N'-(1,6-hexylene)-bis[2-hydroxyundecylamine] (I: R = CH$_3$(CH$_2$)$_8$, R' = H, X = (CH$_2$)$_6$; Z = H) (m.p. 122.6°–129.0° C.).

Hydrogen bromide was bubbled through a solution of N,N'-(1,6-hexylene)-bis[2-hydroxyundecylamine] (5 g.) in methanol (100 ml.). The resulting solid was collected (4.6 g.) and recrystallized from methanol, affording N,N'-(1,6-hexylene)-bis[2-hydroxyundecylamine] dihydrobromide (2.4 g., m.p. 299°–301° C.).

A solution of N,N'-(1,6-hexylene-bis[2-hydroxyundecylamine] (5 g.), glycolic acid (1.66 g.) and methanol was heated until the solids dissolved, then evaporated to dryness. Recrystallization of the solid from acetone afforded N,N'-(1,6-hexylene)bis[2-hydroxyundecylamine] diglycolate (4.6 g., m.p. 88.2°–94.6° C.).

In a similar manner using acetic acid and lactic acid instead of glycolic acid there were obtained, respectively, N,N'-(1,6-hexylene)-bis[2-hydroxyundecylamine] diacetate (m.p. 113°–120.6° C.) and N,N'-(1,6-hexylene)-bis[2-hydroxyundecylamine] dilactate (m.p. 102.0°–104.0° C.).

Using hydrochloric acid, nitric acid, phosphoric acid, sulfamic acid, quinic acid, hydrocinnamic acid, succinic acid, tartaric acid, citric acid, methanesulfonic acid and benzenesulfonic acid, there are obtained, respectively:

N,N'-(1,6-hexylene)-bis[2-hydroxyundecylamine] dihydrochloride;

N,N'-(1,6-hexylene)-bis[2-hydroxyundecylamine] dinitrate;

N,N'-(1,6-hexylene)-bis[2-hydroxyundecylamine] diphosphate;

N,N'-(1,6-hexylene)-bis[2-hydroxyundecylamine] disulfamate;

N,N'-(1,6-hexylene)-bis[2-hydroxyundecylamine] diquinate;

N,N'-(1,6-hexylene)-bis[2-hydroxyundecylamine] dihydrocinnamate;

N,N'-(1,6-hexylene)-bis[2-hydroxyundecylamine] succinate;

N,N'-(1,6-hexylene)-bis[2-hydroxyundecylamine] tartrate;

N,N'-(1,6-hexylene)-bis[2-hydroxyundecylamine] dicitrate;

N,N'-(1,6-hexylene)-bis[2-hydroxyundecylamine] dimethanesulfonate;

and N,N'-(1,6-hexylene)-bis[2-hydroxyundecylamine] dibenzenesulfonate.

Table I shows the results of the antibacterial testing in vitro of N,N'-(1,6-hexylene)-bis[2-hydroxyundecylamine].

Table I

| Microorganism | Bacteriostatic concentration (p.p.m.) | Bactericidal concentration (p.p.m.) |
|---|---|---|
| Staphylococcus aureus | 2.5 | 5 |
| Eberthella typhi | 5 | 5 |
| Clostridium welchii | 10 | 10 |
| Pseudomonas aeruginosa | 7.5 | 25 |

EXAMPLE 2

Condensation of 1-pentene oxide and hexamethylenediamine affords N,N'-(1,6-hexylene)-bis[2-hydroxypentylamine] (I: R = CH$_3$(CH$_2$)$_2$, R' = H, X = (CH$_2$)$_6$, Z = H).

EXAMPLE 3

Condensation of 3-methyl-1-butene oxide and hexamethylenediamine affords N,N'-(1,6-hexylene)-bis[2-hydroxy-3-methylbutylamine] (I: R = (CH$_3$)$_2$CH, R' = H, X = (CH$_2$)$_6$, Z = H).

EXAMPLE 4

Condensation of 1-hexene oxide and hexamethylenediamine affords N,N'-(1,6-hexylene)-bis[2-hydroxyhexylamine] (I: R = CH$_3$(CH$_2$)$_3$, R' = H, X = (CH$_2$)$_6$, Z = H).

EXAMPLE 5

Condensation of 4-methyl-1-pentene oxide and hexamethylenediamine affords N,N'-(1,6-hexylene)-bis[2-hydroxy-4-methylpentylamine] (I: R = (CH$_3$)$_2$CHCH$_2$, R' = H, X = (CH$_2$)$_6$, Z = H).

EXAMPLE 6

Condensation of 3-methyl-1-pentene oxide and hexamethylenediamine affords N,N'-(1,6-hexylene)-bis[2-hydroxy-3-methylpentylamine] (I: R = CH$_3$CH$_2$(CH$_3$)C, R' = H, X = (CH$_2$)$_6$, Z = H).

EXAMPLE 7

Condensation of 3,3-dimethyl-1-butene oxide and hexamethylenediamine affords N,N'-(1,6-hexylene)-bis[2-hydroxy-3,3-dimethylbutylamine] (I: R = (CH$_3$)$_3$C, R' = H, X = (CH$_2$)$_6$, Z = H).

EXAMPLE 8

In a manner similar to that of Example 1, condensation of 1-heptene oxide (71.8 g.) and hexamethylenediamine (32 g.) and recrystallization of the resulting product from ethanol gave N,N'-(1,6-hexylene)-bis[2-hydroxyheptylamine] (I: R = CH$_3$(CH$_2$)$_4$, R' = H, X = (CH$_2$)$_6$, Z = H) (16.5 g., m.p. 131.2°–134.2° C.).

EXAMPLE 9

In a manner similar to that of Example 1, condensation of 1-octene oxide (42 g.) and hexamethylenediamine (19.05 g.) and recrystallization of the resulting product from methanol gave N,N'-(1,6-hexylene)-bis[2-hydroxyoctylamine] (I: R = CH$_3$(CH$_2$)$_5$, R' = H, X = (CH$_2$)$_6$, Z = H) (17.2 g., m.p. 124.0°–127.4° C.).

EXAMPLE 10

In a manner similar to that of Example 1, condensation of 1-nonene oxide (97.4 g.) and hexamethylenediamine (39.8 g.) and recrystallization of the resulting product (67 g.) from ethanol afforded N,N'-(1,6-hexylene)-bis[2-hydroxynonylamine] (I: R = CH$_3$(CH$_2$)$_6$, R' = H, X = (CH$_2$)$_6$, Z = H) (67 g., m.p. 122°–129.2° C.).

Treatment of N,N'-(1,6-hexylene)-bis[2-hydroxynonylamine] (4g.) with lactic acid (2.12 g.) in methanol and recrystallization of the resulting salt from acetone gave N,N'-(1,6-hexylene)-bis[2-hydroxynonylamine] dilactate (3.3 g., m.p. 103.0°–104.6° C.).

EXAMPLE 11

In a manner similar to that of Example 1, condensation of 1-decene oxide (50 g.) and hexamethylenediamine (18.6 g.) and recrystallization of the resulting product from methanol gave N,N'-(1,6-hexylene)-bis[2-hydroxydecylamine] (I: R = CH$_3$(CH$_2$)$_7$, R' = H, X = (CH$_2$)$_6$, Z = H) (25.4 g., m.p. 118.0°–126.8° C.).

EXAMPLE 12

In a manner similar to that of Example 1, condensation of 1-dodecene oxide (50 g.) and hexamethylenediamine (15.8 g.) and recrystallization of the resulting product from ethanol gave N,N'-(1,6-hexylene)-bis[2-hydroxydodecylamine] (I: R = $CH_3(CH_2)_9$, R' = H, X = $(CH_2)_6$, Z = H) (35 g., m.p. 123.6°–128.0° C.).

EXAMPLE 13

Condensation of 1-tridecene oxide and hexamethylenediamine affords N,N'-(1,6-hexylene)-bis[2-hydroxytridecylamine] (I: R = $CH_3(CH_2)_{10}$, R' = H, X = $(CH_2)_6$, Z = H).

EXAMPLE 14

In a manner similar to that of Example 1, condensation of 1-tetradecene oxide (91.8 g.) and hexamethylenediamine (25 g.) and recrystallization of the resulting product (71 g., m.p. 118°–121° C.) from ethanol gave N,N'-(1,6-hexylene)-bis[2-hydroxytetradecylamine] (I: R = $CH_3(CH_2)_{11}$, R' = H, X = $(CH_2)_6$, Z = H) (55.3 g., m.p. 122°–126° C.).

EXAMPLE 15

In a manner similar to that of Example 1, condensation of 1-pentadecene oxide (81.7 g.) and hexamethylenediamine (21 g.) and recrystallization of the resulting product (74.3 g.) from isopropyl alcohol gave N,N'-(1,6-hexylene)-bis[2-hydroxypentadecylamine] (I: R = $CH_3(CH_2)_{12}$, R' = H, X = $(CH_2)_6$, Z = H) (m.p. 117.4°–124.0° C.).

EXAMPLE 16

Condensation of 1-hexadecene oxide and hexamethylenediamine affords N,N'-(1,6-hexylene)-bis[2-hydroxyhexadecylamin] (I: R = $CH_3(CH_2)_{13}$, R' = H, X = $(CH_2)_6$, Z = H).

EXAMPLE 17

Condensation of 1-heptadecene oxide and hexamethylenediamine affords N,N'-(1,6-hexylene)-bis[2-hydroxyheptadecylamine] (I: R = $CH_3(CH_2)_{14}$, R' = H, X = $(CH_2)_6$, Z = H).

EXAMPLE 18

Condensation of vinylcyclobutane oxide and hexamethylenediamine affords N,N'-(1,6-hexylene)-bis[2-hydroxy-2-cyclobutylethylamine] (I:

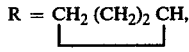

R' = H, X = $(CH_2)_6$, Z = H).

EXAMPLE 19

Condensation of vinylcyclopentane oxide and hexamethylenediamine affords N,N'-(1,6-hexylene)-bis[2-hydroxy-2-cyclopentylethylamine] (I:

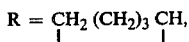

R' = H, X = $(CH_2)_6$, Z = H).

EXAMPLE 20

Condensation of vinylcyclohexane oxide and hexamethylenediamine affords N,N'-(1,6-hexylene)-bis[2-hydroxy-2-cyclohexylethylamine] (I:

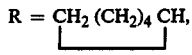

R' = H, X = $(CH_2)_6$, Z = H).

EXAMPLE 21

Condensation of vinylcycloheptane and hexamethylenediamine affords N,N'-(1,6-hexylene)-bis[2-hydroxy-2-cycloheptylethylamine] (I:

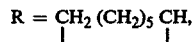

R' = H, X = $(CH_2)_6$, Z = H).

EXAMPLE 22

A. N,N'-(1,6-Hexylene)-bis[2-hydroxyundecylamine] (25.6 g.) was added in portions to a solution of formic acid (98%, 25 ml.) and formaldehyde (60%, 15 ml.) held at 70° C. When the addition was complete the resulting solution was refluxed (9 hr.), then basified with sodium hydroxide solution (35%). The solid was collected and treated with methanolic potassium hydroxide. The mixture was diluted with water and extracted with ether. Concentration of the ether extract and distillation of the residue under vacuum afforded an oil (16 g., b.p. 208°–214° C./0.05 mm.). Hydrogen bromide was bubbled through an ethereal solution of the oil. The resulting solid was recrystallized from ether:isopropyl alcohol, affording N,N'-(1,6-hexylene)-bis[N-methyl-2-hydroxyundecylamine] dihydrobromide (I: R = $CH_3(CH_2)_8$, R' = $CH_3$, X = $(CH_2)_6$, Z = H) (m.p. 186.4°–189.8° C.).

B. Condensation of 1-undecene oxide and N,N'-dimethylhexamethylenediamine and treatment of the resulting product with hydrogen bromide also affords N,N'-(1,6-hexylene)-bis[N-methyl-2-hydroxyundecylamine] dihydrobromide.

Table II shows the results of the in vitro antibacterial testing of N,N'-(1,6-hexylene)-bis[N-methyl-2-hydroxyundecylamine] dihydrobromide.

Table II

| Microorganism | Bacteriostatic concentration (p.p.m.) | Bactericidal concentration (p.p.m.) |
|---|---|---|
| Staphylococcus aureus | 2.5 | 7.5 |
| Eberthella typhi | 5 | 5 |
| Clostridium welchii | 5 | 5 |
| Pseudomonas aeruginosa | 25 | 50 |

EXAMPLE 23

Condensation of 1-undecene oxide and N,N'-diethylhexamethylenediamine affords N,N'-(1,6-hexylene)-bis[N-ethyl-2-hydroxyundecylamine] (I: R = $CH_3(CH_2)_8$, R' = $CH_3CH_2$, X = $(CH_2)_6$, Z = H).

EXAMPLE 24

Condensation of 1-undecene oxide and N,N'-dipropylhexamethylenediamine affords N,N'-(1,6-hexylene)-bis[N-propyl-2-hydroxyundecylamine] (I: R = $CH_3(CH_2)_8$, R' = $CH_3(CH_2)_2$, X = $(CH_2)_6$, Z = H).

EXAMPLE 25

Condensation of 1-undecene oxide and N,N'-di(isopropyl)hexamethylenediamine affords N,N'-(1,6-hexylene)-bis[N-isopropyl-2-hydroxyundecylamine] (I: R = $CH_3(CH_2)_8$, R' = $(CH_3)_2CH$, X = $(CH_2)_6$, Z = H).

EXAMPLE 26

Condensation of 1-undecene oxide and N,N'-dibutyl-hexamethylenediamine affords N,N'-(1,6-hexylene)-bis[N-butyl-2-hydroxyundecylamine] (I: R = $CH_3(CH_2)_8$, R' = $CH_3(CH_2)_3$, X = $(CH_2)_6$, Z = H).

EXAMPLE 27

Condensation of 1-undecene oxide and N,N'-di(isobutyl)hexamethylenediamine affords N,N'-(1,6-hexylene)-bis[N-isobutyl-2-hydroxyundecylamine] (I: R = $CH_3(CH_2)_8$, R' = $(CH_3)_2CHCH_2$, X = $(CH_2)_6$, Z = H).

EXAMPLE 28

Condensation of 1-undecene oxide and N,N'-di(sec-butyl)hexamethylenediamine affords N,N'-(1,6-hexylene)-bis[N-(sec-butyl)-2-hydroxyundecylamine] (I: R = $CH_3(CH_2)_8$, R' = $CH_3CH_2(CH_3)CH$, X = $(CH_2)_6$, Z = H).

EXAMPLE 29

In a manner similar to that of Example 22, methylation of N,N'-(1,6-hexylene)-bis[2-hydroxyheptylamine] (35.7 g.) treatment of a portion (18.0 g.) of the resulting product (35.6 g.) with hydrogen bromide and recrystallization of the resulting salt from acetone gave N,N'-(1,6-hexylene)-bis[N-methyl-2-hydroxyheptylamine] (I: R = $CH_3(CH_2)_4$, R' = $CH_3$, X = $(CH_2)_6$, Z = H) dihydrobromide (15.5 g., m.p. 147.0°–149.0° C.).

EXAMPLE 30

In a manner similar to that of Example 22, methylation of N,N'-(1,6-hexylene)-bis[2-hydroxyoctylamine] (35 g.) and treatment of the resulting product (b.p. 177°–182° C./1 mm.) with hydrogen bromide gave N,N'-(1,6-hexylene)-bis[N-methyl-2-hydroxyoctylamine] (I: R = $CH_3(CH_2)_5$, R' = $CH_3$, X = $(CH_2)_6$, Z = H) dihydrobromide (19.1 g., m.p. 167.0°–168.8° C.).

EXAMPLE 31

In a manner similar to that of Example 22, methylation of N,N'-(1,6-hexylene)-bis[2-hydroxynonylamine] (36 g.) and treatment of the resulting product (25 g., b.p. 172°–176° C./0.05 mm.) with hydrogen bromide gave N,N'-(1,6-hexylene)-bis[N-methyl-2-hydroxynonylamine] (I: R = $CH_3(CH_2)_6$, R' = $CH_3$, X = $(CH_2)_6$, Z = H) dihydrobromide (26.3 g., m.p. 176.0°–177.0° C.).

EXAMPLE 32

In a manner similar to that of Example 22, methylation of N,N'-(1,6-hexylene)-bis[2-hydroxydecylamine] (36.7 g.), treatment of the resulting product (17.5 g., b.p. 204°–206° C./0.03 mm.) with hydrogen bromide and recrystallization of the resulting salt from isopropyl alcohol gave N,N'-(1,6-hexylene)-bis[N-methyl-2-hydroxydecylamine] (I: R = $CH_3(CH_2)_7$, R' = $CH_3$, X = $(CH_2)_6$, Z = H) dihydrobromide (8.4 g., m.p. 186.0°–187.6° C.).

EXAMPLE 33

In a manner similar to that of Example 22, methylation of N,N'-(1,6-hexylene)-bis[2-hydroxydodecylamine] (25 g.), treatment of the resulting product (b.p. 217°–228° C./0.02 mm.) with hydrogen bromide and recrystallization of the resulting salt from isopropyl alcohol gave N,N'-(1,6-hexylene)-bis-[N-methyl-2-hydroxydodecylamine] (I: R = $CH_3(CH_2)_9$, R' = $CH_3$, X = $(CH_2)_6$, Z = H) dihydrobromide (9.6 g., m.p. 197.0°–198.4° C.).

EXAMPLE 34

In a manner similar to that of Example 22, methylation of N,N'-(1,6-hexylene)-bis[2-hydroxytetradecylamine] (30 g.) gave N,N'-(1,6-hexylene)-bis[N-methyl-2-hydroxytetradecylamine] (I: R = $CH_3(CH_2)_{11}$, R' = $CH_3$, X = $(CH_2)_6$, Z = H) as a brown oil (28.2 g.).

EXAMPLE 35

In a manner similar to that of Example 1, condensation of 1-decene oxide (100 g.) and ethylenediamine (19.2 g.) and recrystallization of a portion (20 g.) of the resulting solid (45 g.) from ethanol gave N,N'-ethylenebis[2-hydroxydecylamine] (I: R = $CH_3(CH_2)_7$, R' = H, X = $(CH_2)_2$, Z = H) (13.6 g., m.p. 140.0°–145.8° C.).

EXAMPLE 36

In a manner similar to that of Example 1, condensation of 1-undecene oxide (40 g.) and ethylenediamine (7.07 g.) and two recrystallizations of the resulting solid (14.9 g.) from ethanol gave N,N'-ethylenebis [2-hydroxyundecylamine] (I: R = $CH_3(CH_2)_8$, R' = H, X = $(CH_2)_2$, Z = H) (12.4 g., m.p. 130.2°–137.8° C.).

EXAMPLE 37

In a manner similar to that of Example 1, condensation of 1-dodecene oxide (100 g.) and ethylenediamine (16.3 g.) and recrystallization of part (20 g.) of the resulting product (55.3 g.) from methanol gave N,N'-ethylenebis[2-hydroxydodecylamine] (I: R = $CH_3(CH_2)_9$, R' = H, X = $(CH_2)_2$, Z = H) (13.4 g., m.p. 137.0°–142.0° C.).

EXAMPLE 38

In a manner similar to that of Example 22, methylation of N,N'-ethylenebis[2-hydroxydecylamine] (15 g.) and treatment of the resulting product with hydrogen bromide gave N,N'-ethylenebis[N-methyl-2-hydroxydecylamine] (I: R = $CH_3(CH_2)_7$, R' = $CH_3$, X = $(CH_2)_2$, Z = H) dihydrobromide (4.0 g., m.p. 152.0°–164.0° C.).

EXAMPLE 39

In a manner similar to that of Example 22, methylation of N,N'-ethylenebis[2-hydroxyundecylamine] (30 g.), treatment of the resulting product with hydrogen bromide and recrystallization of the resulting salt from isopropyl alcohol gave N,N'-ethylenebis[N-methyl-2-hydroxyundecylamine] (I: R = $CH_3(CH_2)_8$, R' = $CH_3$, X = $(CH_2)_2$, Z = H) dihydrobromide (12.8 g., m.p. 151.0°–162.0° C.).

EXAMPLE 40

In a manner similar to that of Example 22, methylation of N,N'-ethylenebis[2-hydroxydodecylamine] (35 g.), treatment of the resulting product with hydrogen bromide and recrystallization of the resulting salt from isopropyl alcohol gave N,N'-ethylenebis[N-methyl-2-hydroxydodecylamine] (I: R = $CH_3(CH_2)_9$, R' = $CH_3$, X = $(CH_2)_2$, Z = H) dihydrobromide (4.6 g., m.p. 162.0° C.).

EXAMPLE 41

In a manner similar to that of Example 1, condensation of 1-nonene oxide (120 g.) and 1,3-propanediamine (31.2 g.) and two recrystallizations of the resulting product from methanol gave N,N'-(1,3-propylene)-bis[2-hydroxynonylamine] (I: R = $CH_3(CH_2)_6$, R' = H, X = $(CH_2)_3$, Z = H) (13.2 g., m.p. 107.0°–109.0° C.).

EXAMPLE 42

In a manner similar to that of Example 1, condensation of 1-decene oxide (58 g.) and 1,3-propanediamine (13.8 g.) and three recrystallizations of the resulting product from methanol gave N,N'-(1,3-propylene)-bis[2-hydroxydecylamine] (I: R = $CH_3(CH_2)_7$, R' = H, X = $(CH_2)_3$, Z = H) (8.5 g., m.p. 104.0°–107.6° C.).

EXAMPLE 43

In a manner similar to that of Example 1, condensation of 1-undecene oxide (104.6 g.) and 1,3-propanediamine (22.7 g.) and two recrystallizations of the resulting product from methanol gave N,N'-(1,3-propylene)-bis[2-hydroxyundecylamine] (I: R = $CH_3(CH_2)_8$, R' = H, X = $(CH_2)_3$, Z = H) (29.0 g., m.p. 94.0°–103.0° C.).

EXAMPLE 44

In a manner similar to that of Example 1, condensation of 1-dodecene oxide (100 g.) and 1,3-propanediamine (20.1 g.) and three recrystallizations of the resulting product from isopropyl alcohol gave N,N'-(1,3-propylene)-bis[2-hydroxydodecylamine] (I: R = $CH_3(CH_2)_9$, R' = H, X = $(CH_2)_3$, Z = H) (11.9 g., 96.0°–106.0° C.).

EXAMPLE 45

In a manner similar to that of Example 22, methylation of N,N'-(1,3-propylene)-bis[2-hydroxynonylamine] (14 g.), treatment of the resulting product with hydrogen bromide and two recrystallizations of the resulting salt from acetonitrile gave N,N'-(1,3-propylene)-bis[N-methyl-2-hydroxynonylamine] (I: R = $CH_3(CH_2)_6$, R' = $CH_3$, X = $(CH_2)_3$, Z = H) dihydrobromide (9.1 g., m.p. 175.0°–189.0° C.).

EXAMPLE 46

In a manner similar to that of Example 22, methylation of N,N'-(1,3-propylene)-bis[2-hydroxydecylamine] (21.4 g.), treatment of the resulting product with hydrogen bromide and four recrystallizations of the resulting salt from ethyl acetate-isopropyl alcohol gave N,N'-(1,3-propylene)-bis[N-methyl-2-hydroxydecylamine] (I: R = $CH_3(CH_2)_7$, R' = $CH_3$, X = $(CH_2)_3$, Z = H) dihydrobromide (9.0 g., m.p. 174.2°–184.0° C.).

EXAMPLE 47

In a manner similar to that of Example 22, methylation of N,N'-(1,3-propylene)-bis[2-hydroxyundecylamine] (16 g.), treatment of the resulting product with hydrogen bromide and recrystallization of the resulting salt from acetone gave N,N'-(1,3-propylene)-bis[N-methyl-2-hydroxyundecylamine] (I: R = $CH_3(CH_2)_8$, R' = $CH_3$, X = $(CH_2)_3$, Z = H) dihydrobromide (12.9 g., m.p. 176.0°–189.0° C.).

EXAMPLE 48

Condensation of 1-undecene oxide and 1,4-butanediamine affords N,N'-(1,4-butylene)-bis[2-hydroxyundecylamine] (I: R = $CH_3(CH_2)_8$, R' = H, X = $(CH_2)_4$, Z = H).

EXAMPLE 49

Condensation of 1-undecene oxide and 1,5-pentanediamine affords N,N'-(1,5-pentylene)-bis[2-hydroxyundecylamine] (I: R = $CH_3(CH_2)_8$, R' = H, X = $(CH_2)_5$, Z = H).

EXAMPLE 50

Condensation of 1-heptene oxide and 1,7-heptanediamine affords N,N'-(1,7-heptylene)-bis[2-hydroxyheptylamine] (I: R = $CH_3(CH_2)_4$, R' = H, X = $(CH_2)_7$, Z = H).

EXAMPLE 51

In a manner similar to that of Example 1, condensation of 1-heptene oxide (52 g.) and 1,8-octanediamine (32.8 g.) and two recrystallizations of the resulting product from methanol gave N,N'-(1,8-octylene)-bis[2-hydroxyheptylamine] (I: R = $CH_3(CH_2)_4$, R' = H, X = $(CH_2)_8$, Z = H) (17.2 g., m.p. 128.0°–132.8° C.).

EXAMPLE 52

In a manner similar to that of Example 22, methylation of N,N'-(1,8-octylene)-bis[2-hydroxyheptylamine] (16.9 g.), treatment of the resulting product with hydrogen bromide and two recrystallizations of the resulting salt from isopropyl alcohol gave N,N'-(1,8-octylene)-bis[N-methyl-2-hydroxyheptylamine] (I: R = $CH_3(CH_2)_4$, R' = $CH_3$, X = $(CH_2)_8$, Z = H) dihydrobromide (15.9 g., m.p. 177.0°–190.0° C.).

EXAMPLE 53

Condensation of 1-hexene oxide and 1,9-nonanediamine affords N,N'-(1,9-nonylene)-bis[2-hydroxyhexylamine] (I: R = $CH_3(CH_2)_3$, R' = H, X = $(CH_2)_9$, Z = H).

EXAMPLE 54

In a manner similar to that of Example 1, condensation of 1-hexene oxide (34.8 g.) and 1,10-decanediamine (30 g.) and recrystallization of the resulting product from isopropyl alcohol gave N,N'-(1,10-decylene)-bis[2-hydroxyhexylamine] (I: R = $CH_3(CH_2)_3$, R' = H, X = $(CH_2)_{10}$, Z = H) (8.9 g., m.p. 127.0°–137.0° C.).

EXAMPLE 55

Condensation of 1-pentene oxide and 1,11-undecanediamine affords N,N'-(1,11-undecylene)-bis[2-hydroxypentylamine] (I: R = $CH_3(CH_2)_2$, R' = H, X = $(CH_2)_{11}$, Z = H).

EXAMPLE 56

Condensation of 1-pentene oxide and 1,12-dodecanediamine affords N,N-(1,12-dodecylene)-bis[2-hydroxypentylamine] (I: R = $CH_3(CH_2)_2$, R' = H, X = $(CH_2)_{12}$, Z = H).

EXAMPLE 57

Condensation of 1-undecene oxide and 1-methyl-1,2-ethanediamine affords N,N'-(1,2-propylene)-bis[2-hydroxyundecylamine] (I: R = $CH_3(CH_2)_8$, R' = H, X = $CH(CH_3)CH_2$, Z = H).

EXAMPLE 58

Condensation of 1-undecene oxide and 1,2-dimethyl-1,2-ethanediamine affords N,N'-(2,4-butylene)-bis[2- hydroxyundecylamine] (I: R = CH₃(CH₂)₈, R' = H, X = CH(CH₃)CH(CH₃), Z = H).

EXAMPLE 59

Condensation of 1-pentene oxide and 1,10-dimethyl-1,10-decanediamine affords N,N'-(2,10-dodecylene)-bis[2-hydroxypentylamine] (I: R = CH₃(CH₂)₂, R' = H, X = CH(CH₃)(CH₂)₈CH(CH₃), Z = H).

EXAMPLE 60

Condensation of 1-undecene oxide and 2-methyl-1,4-butanediamine affords N,N'-(2-methyl-1,4-butylene)-bis[2-hydroxyundecylamine] (I: R = CH₃(CH₂)₈, R' = H, X = CH₂CH(CH₃)CH₂CH₂, Z = H).

EXAMPLE 61

In a manner similar to that of Example 1, condensation of 1-octene oxide (50 g.) and 1,4-cyclohexylenebis(methylamine) (27.8 g.) and recrystallization of the resulting product from acetone gave N,N'-(1,4-cyclohexylenebismethyl)-bis[2-hydroxyoctylamine] (I: R = CH₃(CH₂)₅, R' = H, X = CH₂CH(CH₂CH₂)₂CHCH₂, Z = H), (12 g., m.p. 90.0°–96.2° C.).

EXAMPLE 62

In a manner similar to that of Example 1, condensation of 1-decene oxide (two runs, 50 g. each) and 1,4-cyclohexylenebis(methylamine) (22.8 g. each run) and two recrystallizations of the products from acetone gave N,N'-(1,4-cyclohexylenebismethyl)-bis[2-hydroxydecylamine] (R = CH₃(CH₂)₇, R' = H, X = CH₂CH(CH₂CH₂)₂CHCH₂, Z = H) (18.4 g., m.p. 92.0°–98.8° C.).

EXAMPLE 63

In a manner similar to that of Example 1, condensation of 1-decene oxide (96.6 g.) and cis-1,4-cyclohexylenebis(methylamine) (44.2 g.) and two recrystallizations of the resulting product from acetone gave N,N'-(cis-1,4-cyclohexylenebismethyl)bis[2-hydroxydecylamine] (I: R = CH₃(CH₂)₇, R' = H, X = cis-CH₂CH(CH₂CH₂)₂CHCH₂, Z = H) (13.5 g., m.p. 72.6°–77.4° C.).

EXAMPLE 64

In a manner similar to that of Example 1, condensation of 1-decene oxide (98.9 g.) and trans-1,4-cyclohexylenebis(methylamine) (45.2 g.) and recrystallization of the resulting product from acetone gave N,N'-(trans-1,4-cyclohexylenebismethyl)bis[2-hydroxydecylamine] (I: R = CH₃(CH₂)₇, R' = H, X = trans-CH₂CH(CH₂CH₂)₂CHCH₂, Z = H) (23.3 g., m.p. 101.0°–102.8° C.).

EXAMPLE 65

In a manner similar to that of Example 22, methylation of N,N'-(1,4-cyclohexylenebismethyl)-bis[2-hydroxydecylamine] and two recrystallizations of the resulting product from methanol gave N,N'-(1,4-cyclohexylenebismethyl)-bis[N-methyl-2-hydroxydecylamine] (I: R = CH₃(CH₂)₇, R' = H, X = CH₂CH(CH₂CH₂)₂CHCH₂, Z = H) (8.9 g., m.p. 66°–69° C.).

EXAMPLE 66

In a manner similar to that of Example 1, condensation of 1-dodecene oxide (50 g.) and 1,4-cyclohexylenebis(methylamine) (19.3 g.) and recrystallization of the resulting product from methanol gave N,N'-(1,4-cyclohexylenebismethyl)-bis[2-hydroxydodecylamine] (I: R = CH₃(CH₂)₉, R' = H, X = CH₂CH(CH₂CH₂)₂CHCH₂, Z = H) (9.5 g., m.p. 93.0°–96.0° C.).

EXAMPLE 67

Condensation of 1-decene oxide and cyclobutylidenebis(methylamine) affords N,N'-(cyclobutylidenebismethyl)-bis[2-hydroxydecylamine] (I: R = CH₃(CH₂)₇, R' = H, X =

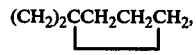
(CH₂)₂CCH₂CH₂CH₂,

Z = H).

EXAMPLE 68

Condensation of 1-decene oxide and 1,2-cycloheptylenebis(methylamine) affords N,N'-(1,2-cycloheptylenebismethyl)bis[2-hydroxydecylamine] (I: R = CH₃(CH₂)₇, R' = H, X =

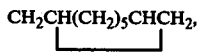
CH₂CH(CH₂)₅CHCH₂,

Z = H).

EXAMPLE 69

Condensation of 1-decene oxide and 1-(aminomethyl)-4-(2-aminoethyl)cyclohexane affords N,N'-[cyclohexylene-1-methyl-4-(2-ethyl)]-bis[2-hydroxydecylamine] (I: R = CH₃(CH₂)₇, R' = H, X = CH₂CH₂CH(CH₂CH₂)₂CHCH₂, Z = H).

EXAMPLE 70

Condensation of 1-decene oxide and 1-(aminomethyl)-4-(1-aminomethyl)cyclohexane affords N,N'-[cyclohexylene-1-methyl-4-(1-ethyl)]-bis[2-hydroxydecylamine] (I: R = CH₃(CH₂)₇, R' = H, X = CH(CH₃)CH(CH₂CH₂)₂CHCH₂, Z = H).

EXAMPLE 71

Condensation of 1-decene oxide and 1-(aminomethyl)-4-(4-aminobutyl)cyclohexane affords N,N'-[cyclohexylene-1-methyl-4-(4-butyl)]-bis[2-hydroxydecylamine] (I: R = CH₃(CH₂)₇, R' = H, X = (CH₂)₄CH(CH₂CH₂)₂CHCH₂, Z = H).

EXAMPLE 72

Condensation of 1-decene oxide and 1,4-phenylenebis(methylamine) affords N,N'-(1,4-phenylenebismethyl)-bis[2-hydroxydecylamine] (I: R = CH₃(CH₂)₇, R' = H, X = 1,4-CH₂C₆H₄CH₂, Z = H).

EXAMPLE 73

Condensation of 1-decene oxide and trans-1,4-(2-butenylene)diamine affords N,N'-[trans-1,4-(2-butylene)]-bis[2-hydroxydecylamine] (I: R = CH₃(CH₂)₇, R' = H, X = trans-CH₂CH=CHCH₂, Z = H).

EXAMPLE 74

Condensation of 1-decene oxide and 1,4-(2-butynylene)diamine affords N,N'-[1,4-(2-butynylene)]-bis[2-hydroxydecylamine] (I: R = CH₃(CH₂)₇, R' = H, X = CH₂C≡CCH₂, Z = H).

4,140,860

EXAMPLE 75

A mixture of N,N'-(1,4-cyclohexylenebismethyl)-bis[N-methyl-2-hydroxydecylamine] (3.6 g.), phenyl isocyanate (1.78 g.), pyridine (seven drops) and benzene (45 ml.) was heated under reflux (for 3 hr.), then filtered. The filtrate was diluted with hexane (10 ml.), and the resulting product (2.4 g.) was recrystallized from methanol, affording N,N'-(1,4-cyclohexylenebismethyl)bis[N-methyl-2-hydroxydecylamine] dicarbanilate (I: R = $CH_3(CH_2)_7$, R' = $CH_3$, X = $CH_2CH(CH_2CH_2)_2CHCH_2$, Z = $CONHC_6H_5$) (m.p. 74°–76° C.).

EXAMPLE 76

Condensation of N,N'-(1,4-cyclohexylenebismethyl)-bis[N-methyl-2-hydroxydecylamine] and o-tolyl isocyanate affords N,N'-(1,4-cyclohexylenebismethyl)-bis[N-methyl-2-hydroxydecylamine] bis(p-methylcarbanilate) (I: R = $CH_3(CH_2)_7$, R' = $CH_3$, X = $CH_2CH(CH_2CH_2)_2CHCH_2$, Z = $CONHC_6H_4CH_3$-o).

EXAMPLE 77

Condensation of N,N'-(1,4-cyclohexylenebismethyl)-bis[N-methyl-2-hydroxydecylamine] and p-bromophenyl isocyanate affords N,N'-(1,4-cyclohexylenebismethyl)-bis[N-methyl-2-hydroxydecylamine] bis(p-bromocarbanilate) (I: R = $CH_3(CH_2)_7$, R' = $CH_3$, X = $CH_2CH(CH_2CH_2)_2CHCH_2$, Z = $CONHC_6H_4Br$-p).

EXAMPLE 78

Condensation of N,N'-(1,4-cyclohexylenebismethyl)-bis[N-methyl-2-hydroxydecylamine] and 4-chloro-o-tolyl isocyanate affords N,N'-(1,4-cyclohexylenebismethyl)-bis[N-methyl-2-hydroxydecylamine] bis(2-methyl-4-chlorocarbanilate) (I: R = $CH_3(CH_2)_7$, R' = $CH_3$, X = $CH_2CH(CH_2CH_2(_2CHCH_2$, Z = $CONHC_6H_3CH_3$-2-Cl-4).

EXAMPLE 79

Condensation of N,N'-(1,4-cyclohexylenebismethyl)-bis[N-methyl-2-hydroxydecylamine] and 5-chloro-2,4-dimethoxyphenyl isocyanate affords N,N'-(1,4-cyclohexylenebismethyl)bis[N-methyl-2-hydroxydecylamine] bis(5-chloro-2,4-dimethoxycarbanilate) (I: R = $CH_3(CH_2)_7$, R' = $CH_3$, X = $CH_2CH(CH_2CH_2)_2CHCH_2$, Z = $CONHC_6H_2(OCH_3)_2$-2,4-Cl-5).

EXAMPLE 80

Condensation of N,N'-(1,4-cyclohexylenebismethyl)-bis[N-methyl-2-hydroxydecylamine] and m-(trifluoromethyl)phenyl isocyanate affords N,N'-(1,4-cyclohexylenebismethyl)bis-[N-methyl-2-hydroxydecylamine] bis[m-(trifluoromethyl)carbanilate] (I: R = $CH_3(CH_2)_7$, R' = $CH_3$, X = $CH_2CH(CH_2CH_2)_2CHCH_2$, Z = $CONHC_6H_4CF_3$-m).

EXAMPLE 81

Condensation of N,N'-(1,4-cyclohexylenebismethyl)-bis[N-methyl-2-hydroxydecylamine] and p-acetamidophenyl isocyanate affords N,N'-(1,4-cyclohexylenebismethyl)-bis[N-methyl-2-hydroxydecylamine] bis(p-acetamidocarbanilate) (I: R = $CH_3(CH_2)_7$, R' = $CH_3$, X = $CH_2CH(CH_2CH_2)_2CHCH_2$, Z = $CONHC_6H_4NHCOCH_3$-p).

EXAMPLE 82

Condensation of N,N'-(1,4-cyclohexylenebismethyl)-bis[N-methyl-2-hydroxydecylamine] and m-nitrophenyl isocyanate affords N,N'-(1,4-cyclohexylenebismethyl)-bis[N-methyl-2-hydroxydecylamine] bis(m-nitrocarbanilate) (I: R = $CH_3(CH_2)_7$, R' = $CH_3$, X = $CH_2CH(CH_2CH_2)_2CHCH_2$, Z = $CONHC_6H_4NO_2$-m).

EXAMPLE 83

Condensation of N,N'-(1,4-cyclohexylenebismethyl)-bis[N-methyl-2-hydroxydecylamine] and p-(methylsulfonyl)phenyl isocyanate affords N,N'-(1,4-cyclohexylenebismethyl)-bis[N-methyl-2-hydroxydecylamine] bis[p-(methylsulfonyl)carbanilate] (I: R = $CH_3(CH_2)_7$, R' = $CH_3$, X = $CH_2CH(CH_2CH_2)_2CHCH_2$, Z = $CONHC_6H_4SO_2CH_3$-p).

Examples 84–90 are N,N'-dioxides of the formula

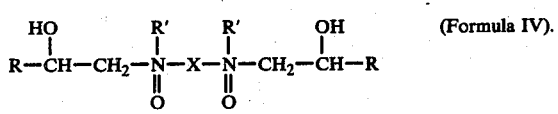

(Formula IV).

EXAMPLE 84

Hydrogen peroxide (30%, 164 ml.) was added dropwise with stirring to a solution of N,N'-(1,6-hexylene)-bis[N-methyl-2-hydroxyundecylamine] (51.6 g.) in alcohol (200 ml.). The temperature was maintained at about 25° C. with cooling during the addition. The solution was allowed to stand overnight at room temperature. A small amount of palladium-on-carbon was added and the mixture was allowed to stand overnight again. The mixture was filtered and the solvents were stripped from the filtrate, leaving an oil. Crystals which separated from an acetone solution of the oil were recrystallized from acetone, affording N,N'-(1,6-hexylene)-bis[N-methyl-2-hydroxyundecylamine]N,N'-dioxide (IV: R = $CH_3(CH_2)_8$, R' = $CH_3$, X = $(CH_2)_6$)(3.2 g., m.p. 168.0°–170.6° C.).

Table II shows the results of the antibacterial testing in vitro of N,N'-(1,6-hexylene)-bis[N-methyl-2-hydroxyundecylamine]N,N'-dioxide.

Table III

| Microorganism | Bacteriostatic concentration (p.p.m.) | Bactericidal concentration (p.p.m.) |
|---|---|---|
| Staphylococcus aureus | 10 | 25 |
| Eberthella typhi | >100 | — |
| Clostridium welchii | 10 | 10 |
| Pseudomonas aeruginosa | 100 | >100 |

EXAMPLE 85

In a manner similar to that of Example 84, oxidation of N,N'-(1,6-hexylene)-bis[N-methyl-2-hydroxyheptylamine] (20.2 g.) and two recrystallizations of the resulting product from acetone gave N,N'-(1,6-hexylene)-bis[N-methyl-2-hydroxyheptylamine] N,N'-dioxide (IV: R = $CH_3(CH_2)_4$, R' = $CH_3$, X = $(CH_2)_6$) (6.0 g., m.p. 148.0°–152.4° C.).

EXAMPLE 86

In a manner similar to that of Example 84, oxidation of N,N'-(1,6-hexylene)-bis[N-methyl-2-hydroxyoctylamine] (30.3 g.) and recrystallization of the resulting product from acetonitrile gave N,N'-(1,6-hexylene)- bis[N-methyl-2-hydroxyoctylamine] N,N'-dioxide (IV: R = $CH_3(CH_2)_5$, R' = $CH_3$, X = $(CH_2)_6$) (26.1 g., m.p. 143.8°–145.5° C.).

EXAMPLE 87

In a manner similar to that of Example 84, oxidation of N,N'-(1,6-hexylene)-bis[N-methyl-2-hydroxynonylamine] and recrystallization of the resulting product from acetonitrile gave N,N'-(1,6-hexylene)-bis[N-methyl-2-hydroxynonylamine] N,N'-dioxide (IV: R = $CH_3(CH_2)_6$, R' = $CH_3$, X = $(CH_2)_6$) (19.3 g., m.p. 155.0°–157.6° C.).

EXAMPLE 88

In a manner similar to that of Example 84, oxidation of N,N'-(1,6-hexylene)-bis[N-methyl-2-hydroxydecylamine] (31.7 g.) and two recrystallizations of the resulting product from acetone-methanol gave N,N'-(1,6-hexylene)-bis[N-methyl-2-hydroxydecylamine] N,N'-dioxide (IV: R = $CH_3(CH_2)_7$, R' = $CH_3$, X = $(CH_2)_6$) (4.0 g., m.p. 162.0°–166.0° C.).

EXAMPLE 89

In a manner similar to that of Example 84, oxidation of N,N'-(1,6-hexylene)-bis[N-methyl-2-hydroxydodecylamine] (40 g.) and two recrystallizations of the resulting product from acetone-methanol gave N,N'-(1,6-hexylene)-bis[N-methyl-2-hydroxydodecylamine] N,N'-dioxide (IV: R = $CH_3(CH_2)_9$, R' = $CH_3$, X = $(CH_2)_6$) (10.4 g., m.p. 163.6°–166.0° C.).

EXAMPLE 90

In a manner similar to that of Example 84, oxidation of N,N'-(1,6-hexylene)-bis[N-methyl-2-hydroxytetradecylamine] (28.2 g.) and two recrystallizations of the resulting product from acetone-methanol gave N,N'-(1,6-hexylene)-bis[N-methyl-2-hydroxytetradecylamine] N,N'-dioxide (IV: R = $CH_3(CH_2)_{11}$, R' = $CH_3$, X = $(CH_2)_6$) (8.8 g., m.p. 150.0°–155.0° C.).

Examples 91–98 are N,N'-diammonium quaternary salts of the formula $$[\text{R}-\overset{\text{HO}}{\underset{\phantom{|}}{\text{CH}}}-\text{CH}_2-\overset{\text{R'}}{\underset{\text{R''}}{\text{N}}}-\text{X}-\overset{\text{R'}}{\underset{\text{R''}}{\text{N}}}-\text{CH}_2-\overset{\text{OH}}{\underset{\phantom{|}}{\text{CH}}}-\text{R}]^{++}[\text{Y}]^{--} \quad \text{(Formula V)}.$$

EXAMPLE 91

A mixture of N,N'-(1,6-hexylene)-bis[N-methyl-2-hydroxyundecylamine] (10 g.), methyl chloride (34 g.) and acetonitrile (30 ml.) was heated in a bomb (60°–65° C., 4 hr.). The resulting product (3.6 g.) was recrystallized from acetonitrile affording N,N'-(1,6-hexylene)-bis[N,N-dimethyl-2-hydroxyundecylammonium]dichloride (V: R = $CH_3(CH_2)_8$, R' = R" = $CH_3$, X = $(CH_2)_6$, Y = Cl) (7.0 g., m.p. 171.0°–174.8° C.).

Table IV shows the results of the antibacterial testing in vitro of N,N'-(1,6-hexylene)-bis[N,N-dimethyl-2-hydroxyundecylammonium]dichloride.

Table IV

| Microorganism | Bacteriostatic concentration (p.p.m.) | Bactericidal concentration (p.p.m.) |
|---|---|---|
| Staphylococcus aureus | 2.5 | 2.5 |
| Eberthella coli | 50 | 50 |
| Pseudomonas aeruginosa | 50 | >100 |
| Proteus vulgaris | >100 | |

Table IV-continued

EXAMPLE 92

In a manner similar to that of Example 91, quaternerization of N,N'-(1,6-hexylene)-bis[N-methyl-2-hydroxydecylamine] (two runs, 10 g. each) with methyl chloride (40 ml. one run, 28 g. other run) and recrystallization of the combined products from acetonitrile gave N,N'-(1,6-hexylene)-bis[N,N-dimethyl-2-hydroxydecylammonium]dichloride (V: R = $CH_3(CH_2)_7$, R' = R" = $CH_3$, X = $(CH_2)_6$, Y = Cl) (18.7 L g., m.p. 171.0°–174.0° C.).

EXAMPLE 93

Quaternerization of N,N'-(1,6-hexylene)-bis[N-methyl-2-hydroxydecylamine] with methyl iodide affords N,N'-(1,6-hexylene)-bis[N,N-dimethyl-2-hydroxydecylammonium]dichloride (V: R = $CH_3(CH_2)_7$, R' = R" = $CH_3$, X = $(CH_2)_6$, Y = I).

EXAMPLE 94

Quaternerization of N,N'-(1,6-hexylene)-bis[N-methyl-2-hydroxydecylamine] with ethyl p-toluenesulfonate affords N,N'-(1,6-hexylene)-bis[N-ethyl-N-methyl-2-hydroxydecylammonium] bis(p-toluenesulfonate) (V: R = $CH_3(CH_2)_7$, R" = $CH_3$, R" = $CH_3CH_2$, X = $(CH_2)_6$, Y = $SO_3C_6H_4CH_3$-p).

EXAMPLE 95

Quaternerization of N,N'-(1,6-hexylene)-bis[N-methyl-N-propyl-2-hydroxydecylamine] with propyl bromide affords N,N'-(1,6-hexylene)-bis[N-methyl-N-propyl-2-hydroxydecylammonium] dibromide (V: R = $CH_3(CH_2)_7$, R' = $CH_3$, R" = $CH_3(CH_2)_2$, X = $(CH_2)_6$, Y = Br).

EXAMPLE 96

Quaternerization of N,N'-(1,6-hexylene)-bis[N-methyl-2-hydroxydecylamine] with isobutyl iodide affords N,N'-(1,6-hexylene)-bis[N-isobutyl-N-methyl-2-hydroxydecylammonium] diiodide (V: R = $CH_3(CH_2)_7$, R' = $CH_3$, R" = $(CH_3)_2CHCH_2$, X = $(CH_2)_6$, Y = I).

EXAMPLE 97

In a manner similar to that of Example 91, quaternerization of N,N'-(1,6-hexylene)-bis[N-methyl-2-hydroxydodecylamine] (10 g.) with methyl chloride (34 g.) and recrystallization of the resulting product from acetonitrile gave N,N'-(1,6-hexylene)-bis[N,N-dimethyl-2-hydroxydodecylammonium]dichloride (V: R = $CH_3(CH_2)_9$, R' = R" = $CH_3$, X = $(CH_2)_6$, Y = Cl)(8.5 g., m.p. 176.6°–180.0° C.).

EXAMPLE 98

A mixture of N,N'-(1,6-hexylene)-bis[N-methyl-2-hydroxyheptylamine] (5 g.), benzyl bromide (4.7 g.) and hexane (60 ml.) was heated under reflux (for 5 hr.). Acetonitrile (20 ml.) was added and refluxing was continued (for 5 hr.). The solvents were stripped and the residue was recrystallized from ethylene dichloride, affording N,N'-(1,6-hexylene)-bis[N-benzyl-N-methyl- 2-hydroxyheptylammonium]dibromide (V: R = CH$_3$(CH$_2$)$_4$, R' = CH$_3$, R" = C$_6$H$_5$CH$_2$, X = (CH$_2$)$_6$, Y = Br) (3.5 g., m.p. 127.0°–129.0° C.)

We claim:

1. N,N'-(X)-bis[N-(R')-2-(R)-2-(ZO)-ethylamine] of the formula

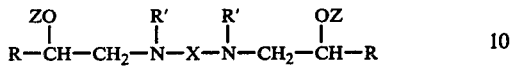

wherein:
R is alkyl of three to fifteen carbon atoms or cycloalkyl of four to seven ring carbon atoms;
R' is a tertiary alkyl of one to four carbon atoms;
X is alkylene of two to twelve carbon atoms with bonds to the nitrogen atoms at different carbon atoms or X'—Y—X", wherein R' and X" are alkylene of one to four carbon atoms with bonds to Y and to the nitrogen atoms at the same or different carbon atoms and Y is cycloalkylene of four to seven ring carbon atoms with bonds to X' and X" at the same or different carbon atoms, phenylene, vinylene or ethynylene;
the sum of the number of carbon atoms of R and X is at least nine;
Z is N-phenylcarbamoyl or N-phenylcarbamoyl substituted in the benzene ring by one to three members selected from the group consisting of a tertiary alkyl of one to four carbon atoms, halo and a tertiary alkoxy of one to four carbon atoms or by a member selected from the group consisting of trifluoromethyl, acetamido, nitro and methylsulfonyl; or
an acid-addition salt thereof.

2. N,N'-(X)-bis[N-(R')-2-(R)-2-(ZO)-ethylamine] wherein:
R is alkyl of three to fifteen carbon atoms;
R' is a tertiary alkyl of one to four carbon atoms;
X is X'—Y—X", wherein X' and X" are alkylene of one to four carbon atoms with bonds to Y and to the nitrogen atoms at the same or different carbon atoms and Y is cycloalkylene of four to seven ring carbon atoms with bonds to X' and X" at the same or different carbon atoms; and
Z is N-phenylcarbamoyl according to claim 1.

3. N,N'-(1,4-cyclohexylenebismethyl)-bis[N-methyl-2-hydroxydecylamine] dicarbanilate according to claim 2.

* * * * *

UNITED STATES PATENT AND TRADEMARK OFFICE
CERTIFICATE OF CORRECTION

PATENT NO. : 4,140,860
DATED : February 20, 1979
INVENTOR(S) : Guy D. Diana and Royal A. Cutler It is certified that error appears in the above-identified patent and that said Letters Patent are hereby corrected as shown below:

In the title "HYDROXYAMIDE" should read -- HYDROXYAMINE --.

Under Related U.S. Appln. Data, first line, "July 15" should read -- Sept. 15 --; third line, "4,085,114" should read -- 4,085,144 --.

Column 1, line 10                      "4,085,114" should read -- 4,085,144 --.

Signed and Sealed this

Twenty-ninth Day of May 1979

[SEAL]

Attest:

RUTH C. MASON
Attesting Officer

DONALD W. BANNER
Commissioner of Patents and Trademarks